United States Patent [19]

Adlerberth et al.

[11] Patent Number: 6,159,465

[45] Date of Patent: *Dec. 12, 2000

[54] EPITHELIAL ADHESIVE LACTOBACILLI

[75] Inventors: Ingegerd Adlerberth, Göteborg; Siv Ahrne, Bjärred; Bengt Jeppsson, Lund; Marie-Louise Johansson, Lund; Göran Molin, Lund; Agnes Wold, Göteborg, all of Sweden

[73] Assignee: Probi AB, Lund, Sweden

[ * ] Notice: This patent issued on a continued prosecution application filed under 37 CFR 1.53(d), and is subject to the twenty year patent term provisions of 35 U.S.C. 154(a)(2).

[21] Appl. No.: 08/913,618

[22] PCT Filed: Mar. 25, 1996

[86] PCT No.: PCT/SE96/00372

§ 371 Date: Sep. 23, 1997

§ 102(e) Date: Sep. 23, 1997

[87] PCT Pub. No.: WO96/29083

PCT Pub. Date: Sep. 26, 1996

[30] Foreign Application Priority Data

Mar. 23, 1995 [SE] Sweden .................................. 9501056

[51] Int. Cl.[7] .............................. A01N 63/00; C12N 1/20

[52] U.S. Cl. ...................................... 424/93.45; 435/252.9

[58] Field of Search ................................. 435/252.9, 853, 435/857; 424/93.45

[56] References Cited

U.S. PATENT DOCUMENTS 5,474,932 12/1995 Bengmark ............................ 435/259.9
5,587,314 12/1996 Bengmark ............................ 435/259.9

FOREIGN PATENT DOCUMENTS 0203586 12/1986 European Pat. Off. .
WO 9301823 2/1993 WIPO .
WO 9309793 5/1993 WIPO .

*Primary Examiner*—Irene Marx
*Attorney, Agent, or Firm*—Oblon, Spivak, McClelland, Maier & Neustadt, P.C.

[57] ABSTRACT

The invention refers to the use of *Lactobacillus plantarum* 299v having a mannose-specific adhesin for the preparation of a pharmaceutical composition inhibiting the binding of pathogenic bacteria expressing mannose-specific adhesins to the epithelial cell surface. The strain of *Lactobacillus plantiarum* which can be used in the invention adheres to D-mannose-coated agarose beads. The invention also refers to the use of said strain for the preparation of a pharmaceutical composition to be used in prophylatic and/or curative treatment of bacterial translocation, gastroenteritis and other diseases caused by pathogenic bacteria expressing mannose-specific adhesins.

5 Claims, 1 Drawing Sheet

EPITHELIAL ADHESIVE LACTOBACILLI

This application is a 371 of PCT/S96/00372 filed Mar. 25, 1996.

The present invention refers to Lactobacillus strains which have the ability to adhere to epithelial cell surfaces, especially in the human intestinal mucosa, and which can be used for the prophylactic and/or curative treatment of bacterial disturbances caused by pathogenic bacteria adhering to the epithelial cell in a similar way.

BACKGROUND OF THE INVENTION

The indigenous microbiota is one of the major defense mechanisms that protect the human or animal body against colonization by invading bacteria. Immunosuppressed, antibiotic treated and parenterally fed patients are at a risk of infectious diseases like sepsis, meningitis or urinary tract infections produced by spread of bacteria mainly deriving form the normal fecal population. One mechanism behind this process can be bacterial translocation, which is defined as the passage of viable bacteria from the gastrointestinal tract to the mesenteric lymph nodes and other organs.

Blood poisoning, sepsis, is still a very common surgical complication in connection with abdominal surgery with a high death-rate. Bacteria or bacterial products may penetrate the malfunctioning intestinal wall and infect or induce malfunction in other remote organs, such as lungs, liver, heart etc. and this leads to multiple organ dysfunction or the so called intensive-care-disease. These patients are today treated by administration of antibiotics and surgical treatment of the abscess to the extent it could be located. At present antibiotics are conventionally administered before intestinal surgery in order to reduce the risk of postoperative infections and illness caused thereby. However, the treatment with antibiotics is associated with destruction of the normal intestinal flora and overgrowth with still more pathogenic bacteria.

These findings have led to an increased interest for microbial species which can beneficially affect the microbial balance of the host, e.g. by producing antimicrobial components or by competitive growing. Lactobacillus have been among the most studied species, and have in certain instances been shown to counteract the proliferation of pathogens.

Bacteria residing in the intestine may cause diseases in the colonized host such as diarrhoea in the intestines, or by secondarily colonizing normally sterile sites, such as the urinary tract, giving a urinary tract infection, or the blood stream, giving sepsis.

Pathogenic bacteria differ from those who do not provoke disease by the possession of so called virulence factors. An important virulence factor is the capacity to adhere to host cell carbohydrate receptor molecules. This is an important step, both because it enables colonization, and because it enables the delivery of toxins and other inflammatogenic substances in close proximity to the host cells. If delivered by an adherent bacterium, these toxic substances reach much higher concentrations locally than they would if they were secreted e.g. by bacteria residing in the intestinal lumen.

Bacteria causing urinary tract infection include *Escherichia coli*, Enterobacter, Klebsiella and Proteus, which all belong to the family Enterobacteriaceae. A majority of these bacteria possess type 1 fimbriae which confer the ability to adhere to mannose-containing receptors, for example on human vaginal epithelia cells and to the urinary slime protein Tamm-Horsefall protein. Type 1 fimbriae have been shown to be a virulence factor for cystitis, which can depend both on an increased ability to ascend into the urinary tract conferred by binding to vaginal and periurethral epithelial cells, as well as on an increased irritative effect caused by binding to epithelial cells in the urinary tract. [Thus only bacteria with type 1 fimbriae were able to induce a cytokine response, that is inflammation, in cultured urinary epithelial cells.]

Bacteria causing diarrhoea include Salmonella and Shigella, but intestinal overgrowth of Klebsiella or Enterobacter have also been associated with diarrhoea in young infants. It has been shown in the mouse that type 1 fimbriae are a virulence factor for diarrheal disease caused by Salmonella. It is also likely that type 1 fimbriae also facilitate colonization of other bacteria and enhance the delivery of toxic substances close to the epithelium, thereby causing diarrhoea.

PRIOR ART

EP-A2-0 199 535 describes a biologically pure culture of *Lactobacillus acidophilus*, ATCC accession No. 53 103, isolated from human faeces, being able to adhere to mucosal cells in tests in vitro. *L. acidophilus* manages the passage through the upper part of the gastro-intestinal tract well. An adherence in vivo has, however, not been demonstrated.

WO 89/05849 describes lactic acid bacteria isolated from the gastro-intestinal tract in pigs and selected by means of, among others, adhesion to gastro-intestinal epithelial cells from pigs in vitro and tolerance against acid and bile. Said bacteria can be used for the fermentation of milk which then can be given to piglets to prevent or treat i.a. *E. coli* diarrhoea.

WO 93/01823 refers to a process for isolation of strains of Lactobacillus having the ability to become established on the human intestinal mucosa in vivo and also to remain thereon after oral administration for at least 10 days. Said application especially refers to two new Lactobacillus strains, which have been deposited according to the Budapest Agreement at the DSM—Deutsche Sammlung von Mikroorganismen und Zellkulturen GmbH-, Braunschweig, Germany on Jul. 2, 1991, that is

| Lactobacillus plantarum 299 | DSM 6595 |
| Lactobacillus casei ssp. rhamnosus 271 | DSM 6594 | as well as variants thereof to be used for the prophylaxis or treatment of bacterial infections in the gastro-intestinal tract, especially substituting antibiotics in connection with surgical operations.

SE 463 598 refers to a preparation for increasing the adherence of bacteria to the gastro-intestinal tract, which preparation is said to contain an adhesion promoting protein, named adhesin, obtained from Lactobacillus.

WO90/09398 refers to products for inhibiting the adhesion, growth and/or survival of pathogens. Said products are *Lactobacillus metabolites* which inhibit pathogens, such as *Escherichia coli*, Clostridium, Salmonella, Campylobacter and Streptococcus strains.

DESCRIPTION OF THE INVENTION

It has now surprisingly been found that certain strains of Lactobacillus adhere to D-mannose coated agarose beads, which ability is correlated with an ability to agglutinate erythrocytes in a mannose-sensitive manner, as well as an ability to adhere to the human colonic epithelial cell line HT-29 in a manner inhibitable by methyl-α-D-mannoside. Periodate treatment of HT-29 cells abolished the mannose-sensitive adherence, confirming that the cell-bound receptor was of carbohydrate nature. Proteinase K treatment of the bacteria also abolished adherence, indicating that the binding involved protein structures on the bacterial cell surface. The adhesive part of the Lactobacillus, the adhesin, is therefore believed to adhere to mannose-containing receptors on the epithelial cell surface. This adherence seems to be related to the capacity of these bacteria to counteract pathogenic bacteria and stimulate host defence mechanisms.

In particular this adherence brings about an ability to decrease the translocation of pathogenic or potentially pathogenic bacteria over intact intestinal epithelium, to inhibit the adherence of potentially pathogenic bacteria directly to the epithelial cell surface, thereby reducing their ability to deliver toxic and inflammatory substances to the mucosa, and to decrease the inflammatory damage to the intestine caused by non-specific irritants by creating a microenvironment favourable for the reconstruction of the mucosa. A close association with the epithelial cells may also increase the ability of the bacterium to interact with the immune system. These Lactobacillus strains may for instance trigger activation of phagocytes and stimulate the antigen-presenting cells bringing about enhanced immunity.

The present invention refers to the use of a *Lactobacillus plantarum* having a mannose-specific adhesin for the preparation of a pharmaceutical composition inhibiting the binding of pathogenic bacteria expressing mannose-specific adhesins to the epithelial cell surface. By this their ability to invade or deliver toxic and inflammatogenic substances on the mucosa will be reduced.

Mannose-specific adhesins have been described in a variety of gram negative bacteria, including members of the Enterobacteriaceae family, such as *E. Coli*, Klebsiella, Shigella and Salmonella species, *Pseudomonas echinoides, Vibrio cholerae* and *Vibrio parahaemolyticus*.

The optimal receptor for the mannose-specific adhesin of *E. coli* has been defined and it is known that it contains the sequence mannoseα1-4mannoseβ which occur in mammalian glyco-proteins. The exact receptor structure of the mannose-specific adhesins of other enterobacterial species has not yet been defined, nor has the receptor structure of the mannose-specific adhesin of the *Lactobacillus plantarum* strains. It is, however, believed that the receptor should contain a Manα1-2Man sequence. It is likely that mannose-specific *L. plantarum* will have a more pronounced inhibitory effect on bacteria binding to mannose-containing receptors as compared to their effect on bacteria binding to other receptor structures.

The invention especially refers to the use of a *Lactobacillus plantarum* which adheres to D-mannose-coated agarose beads for the preparation of a pharmaceutical composition inhibiting the binding of pathogenic bacteria expressing mannose-specific adhesins to the epithelial cell surface.

Preferred strains of Lactobacillus plantarum are:

| | |
|---|---|
| Lactobacillus plantarum 299 | DSM 6595 |
| Lactobacillus plantarum 299v | DSM 9843 |
| Lactobacillus plantarum 79 | |
| Lactobacillus plantarum 105 | |
| Lactobacillus plantarum 107. | |

The invention also refers to the use of *Lactobacillus plantarum* having a mannose-specific adhesin in combination with a conventional carrier for the preparation of a pharmaceutical composition inhibiting the binding of pathogenic bacteria expressing mannose-specific adhesins to the epithelial cell surface for the prophylactic or curative treatment of bacterial disturbances.

Two factors seem to be crucial for the exertion of ecological effects of Lactobacilli. The first is the capacity to colonize the intestine, that is to survive in high numbers for a period of time after the last administration of live bacteria. This property may be important for the ability of the Lactobacilli to suppress the growth and proliferation of pathogenic bacteria, but not sufficient. The second is the capacity to bind directly to intestinal epithelial cells. This may be one of the factors that promotes colonization, but is not a prerequisite for colonization. The ability to adhere to the epithelium does not guarantee that the strain is able to colonize.

The invention additionally refers to the use of a *Lactobacillus plantarum* having a mannose-specific adhesin as well as the ability to colonize human intestinal mucosa for the preparation of a pharmaceutical composition inhibiting the adherence of pathogenic bacteria expressing mannose-specific adhesins to the human intestinal epithelial cell surface.

Pathogenic enteric bacteria expressing mannose-specific type 1 fimbriae especially belong to Klebsiella, Enterobacter, Proteus, Salmonella and Shigella spp., e.g. *Klebsiella pneumoniae, Salmonella typhimurium,* and *Shigella flexneri* and *Escherichia coli*.

The capacity to adhere directly to epithelial cells may be important for the Lactobacillus strains to decrease translocation and induction of mucosal inflammation by pathogenic bacteria since the Lactobacilli occupy the ecological niche close to the epithelium. A close association with the epithelium also enables Lactobacilli to change the microenvironment which directly affects the intestinal epithelial cell, thereby promoting repair after damage caused by irritating agents.

The invention also refers to the use of a *Lactobacillus plantarum* as described above for prophylactic and/or curative treatment of translocation of pathogenic or potentially pathogenic bacteria over intact intestinal epithelium. Translocation denotes the passage of viable bacteria over the intestinal epithelium so that they are recovered e.g. from mesenteric lymph nodes, blood or other organs.

Conventional carriers for a pharmaceutical composition for the prophylactic or curative treatment of bacterial disturbances in the intestines are for example physiologically acceptable substrates fermented by the bacterium in question, as well as foodstuffs of various kinds, especially based on starch or milk, but also inert solid or liquid substances, such as saline or water. A suitable substrate should contain liquid or solid fibres which are not resorbed in the gastro-intestinal tract and which when fermented with Lactobacillus form carboxylic acids. As an example of suitable, starch-containing substrates can be mentioned cereals, such as oats and wheat, corn, root vegetables such as potatoes and certain fruits such as green bananas.

A preferred substrate for the composition according to the invention, which also gives the composition an excellent nutritional value, is a nutrient solution based on oatmeal, for instance as described in WO 89/08405.

The composition according to the invention can be administered in any suitable way, preferably orally or rectally, for example in the form of enema. It can also be administered enterally through a catheter inserted in the intestines via the stomach or directly in the intestines. Tests have shown that the effect is improved if dietary fibres in the form of for example oatmeal gruel or of β-glucans are supplied. The treatment should take place once or several times daily for a period of 1–2 weeks.

The invention also refers to the use of a *Lactobacillus plantarum* as described above for the preparation of a pharmaceutical composition inhibiting the adherence of pathogenic bacteria expressing mannose-specific adhesins, especially *E. coli* expressing type 1 fimbriae, to human vaginal and urethral epithelial cells.

ISOLATION OF LACTOBACILLUS STRAINS

Figure 1:
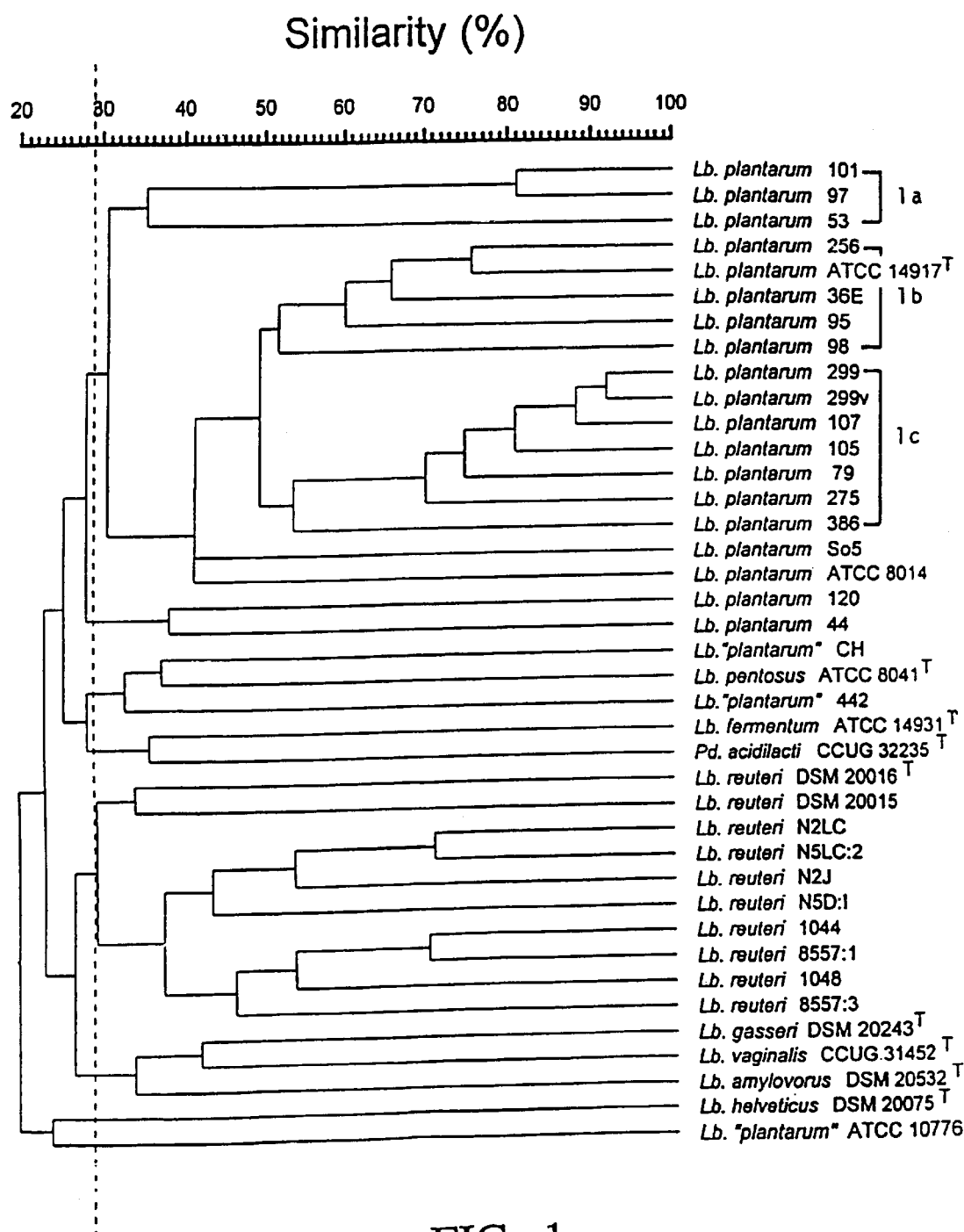
FIG. 1 is a dendrogram showing the similarity in % between different tested strains of Lactobacillus which have been characterized by the REA-method, based on the Pearson product moment correlation coefficient and UPGMA.

Strains of Lactobacillus have been sampled from human mucosa. Biopsies from different parts of colon were taken by means of enteroscopy and pieces of the intestinal mucosa from the small intestine, that is jejunum and ileum, were removed in connection with surgical operations. The mucosa samples were immediately placed in a special medium (0.9% NaCl, 0.1% pepton, 0.1% Tween 80 and 0.02% cystine; all values refer to % by weight/volume), homogenized in an ultrasonic bath for 2 minutes and stirred for 1 minute before being placed on Rogosa agar (Difco Laboratories, Detroit, Mich., USA). The plates were incubated anaerobically at 37° C. for 2 d (Gas Pak Anaerobic System, BBL). One to three colonies were picked at random from each plate and were grown in pure cultures 5 to 9 times on Rogosa agar and kept as dense cultures in a frozen buffer at −80° C. By this procedure the strains *Lactobacillus plantarum* 299 and 299v, as well as 105, 275 and 386; *Lactobacillus fermentum* 8704:3; *Lactobacillus reuteri* 108, 8557:1, 8557:3; *Lactobacillus rhamnosus* 271; *Lactobacillus agilis* 294 were isolated. In a similar way lactobacillus strains were isolated from rat and pig intestines, that is *Lactobacillus reuteri* R2LC and 1063, 1068 and 1044, respectively.

Lactobacillus strains were also isolated from *Nigerian ogi* or *pito* in the following way. The original sample was treated in an ultrasonic bath for 5 minutes and mixed on a Vortex for 2 minutes, diluted and then incubated on *Rogosa agar* (Difco) for 3 d at 37° C. Randomly picked bacterial colonies were tested. By this procedure the strains *Lactobacillus plantarum* 79 and 107, 125, 98, 53, 97M2, 97, 101, 120 and 44 were obtained.

Lactobacillus strains were also isolated from silage, that is *Lactobacillus plantarum* 36E, 256 and ATCC8014. So5 is a *Lactobacillus plantarum* starter culture obtained from Sockerbolaget, Arlöv and *Lactobacillus reuteri* BR is the strain commercially used in BRA-milk (Arla Ekonomisk Förening, Stockholm, Sweden).

Identification of Strains

ATCC 14917$^T$ and DSM 20016$^T$ are the type strains for *Lactobacillus plantarum* and *Lactobacillus reuteri*, respectively. A type strain defines the species and should be marked with a $^T$. All other strains having a DNA:DNA homology of more than 70% to a particular type strain are said to belong to that particular species.

In the International Journal of Systematic Bacteriology (1995) 45:670–675 Johansson, M-L, et al. describe the classification of the isolated strains by means of restriction endonuclease analysis of the total chromosomal DNA. In the "fingerprint" obtained, genetic groups or clusters are formed reflecting the similarity in the total pattern on comparison. According to this analysis method the *Lactobacillus plantarum* strains could be divided into different genetic groups 1a, 1b, 1c, as can be seen on FIG. 1. The strains in cluster 1c all have a similarity to *L. plantarum* 299 of >50%, and the strains 299v, 107, 105 and 79 have a similarity of >70%.

The strains 299 and 299v, which were both isolated from healthy human intestinal mucosa, have been deposited at the Deutsche Sammlung von Mikroorganismen und Zellkulturen GmbH Mascheroder Weg 1B, D-3300 Branschweig, Germany on Jul. 2, 1991 and Mar. 16, 1995, respectively, and have been given the deposition numbers DSM 6595 (299) and DSM 9843 (299v).

Phenotypic Identification

The strains 299, 299v, 79, 105 and 107 are Gram positive, catalase-negative rods growing on Rogosa agar at pH 5.5 and capable of producing lactic acid from glucose anaerobically. The ability of the strains to ferment different carbohydrates is shown in Table 1. The tests have been carried out by means of the API 50 CH in accordance with the instructions of the manufacturer.

Phenotypically the strains can be identified as *Lactobacillus plantarum*.

TABLE 1

Fermentation patterns of strains *L. plantarum* 299, *L. plantarum* 299v, *L. plantarum* 107, *L. plantarum* 105 and *L. plantarum* 275 on API 50CH at 30° C. and 37° C.

| | L. plantarum 299 | | L. plantarum 229v | | L. plantarum 107 | | L. plantarum 105 | | L. plantarum 79 | |
|---|---|---|---|---|---|---|---|---|---|---|
| | 30° C. | 37° C. | 30° C. | 37° C. | 30° C. | 37° C. | 30° C. | 37° C. | 30° C. | 37° C. |
| Glycerol | − | − | − | − | − | − | − | − | − | − |
| Erythritol | − | − | − | − | − | − | − | − | − | − |
| D-arabinose | − | − | − | − | − | − | − | − | − | − |
| L-arabinose | + | + | + | + | + | + | + | + | + | + |
| Ribose | + | + | + | + | + | + | + | + | + | + |
| D-xylose | − | − | − | − | − | − | − | − | − | − |
| L-xylose | − | − | − | − | − | − | − | − | − | − |
| Adonitol | − | − | − | − | − | − | − | − | − | − |
| β-methyl-xyloside | − | − | − | − | − | − | − | − | − | − |
| Galactose | + | + | + | + | + | + | + | + | + | + |
| D-glucose | + | + | + | + | + | + | + | + | + | + |
| D-fructose | + | + | + | + | + | + | + | + | + | + |

TABLE 1-continued

Fermentation patterns of strains L. plantarum 299, L. plantarum 299v, L. plantarum 107, L. plantarum 105 and L. plantarum 275 on API 50CH at 30° C. and 37° C.

| | L. plantarum 299 | | L. plantarum 229v | | L. plantarum 107 | | L. plantarum 105 | | L. plantarum 79 | |
|---|---|---|---|---|---|---|---|---|---|---|
| | 30° C. | 37° C. | 30° C. | 37° C. | 30° C. | 37° C. | 30° C. | 37° C. | 30° C. | 37° C. |
| D-mannose | + | + | + | + | + | + | + | + | + | + |
| L-sorbose | − | − | − | − | − | − | − | − | − | − |
| Rhamnose | − | − | − | − | − | − | − | − | − | − |
| Dulcitol | − | − | − | − | − | − | − | − | − | − |
| Inositol | − | − | − | − | − | − | − | − | − | − |
| Mannitol | + | + | + | + | + | + | + | + | + | + |
| Sorbitol | + | + | + | + | + | + | + | + | + | + |
| α-methyl-D-mannoside | + | + | + | + | + | + | + | + | + | + |
| α-methyl-D-glucoside | − | − | − | − | − | − | − | − | − | − |
| N-acetyl-glucoseamine | + | + | + | + | + | + | + | + | + | + |
| Amygdaline | + | + | + | + | + | + | + | + | + | + |
| Arbutin | + | + | + | + | + | + | + | + | + | + |
| Aesculin | + | + | + | + | + | + | + | + | + | + |
| Salicine | + | + | + | + | + | + | + | + | + | + |
| Cellobiose | + | + | + | + | + | + | + | + | + | + |
| Maltose | + | + | + | + | + | + | + | + | + | + |
| Lactose | + | + | + | + | + | + | + | + | + | + |
| Melibiose | + | + | + | + | + | + | + | + | + | + |
| Saccharose | + | + | + | + | + | + | + | + | + | + |
| Trehalose | + | + | + | + | + | + | + | + | + | + |
| Inulin | − | − | − | − | − | − | − | − | − | − |
| Melezitose | + | + | + | + | + | + | + | + | + | + |
| D-raffinose | − | − | + | − | + | − | − | − | − | − |
| Starch | − | − | − | − | − | − | − | − | − | − |
| Glycogen | − | − | − | − | − | − | − | − | − | − |
| Xylitol | − | − | − | − | − | − | − | − | − | − |
| β-gentiobiose | + | + | + | + | + | + | + | + | + | + |
| D-turanose | + | + | + | + | + | + | + | + | + | + |
| D-lyxose | − | − | − | − | − | − | − | − | − | − |
| D-tagarose | − | − | − | − | − | − | − | − | − | − |
| D-fucose | − | − | − | − | − | − | − | − | − | − |
| L-fucose | − | − | − | − | − | − | − | − | − | − |
| D-arabitol | − | − | + | − | + | − | + | − | + | − |
| L-arabitol | − | − | − | − | − | − | − | − | − | − |
| Gluconate | + | + | + | + | + | + | + | + | + | + |
| 2-keto-gluconate | − | − | − | − | − | − | − | − | − | − |
| 5-keto-gluconate | − | − | − | − | − | − | − | − | − | − |

Plasmid Profiling

The strains were tested according to the method described by Chassy et al (1976) as to the contents of plasmids. *Lactobacillus plantarum* 299, 299v, 79 and 105 had identical plasmid profiles, i.e. five plasmids of 4, 9, 15, 21 and >30 MDa. *Lactobacillus plantarum* 107 had three plasmids of 4, 15 and 21 MDa.

Cultivation of *Lactobacillus plantarum* 299

An inoculate from a freezer of −80° C. is added to 50 ml Lactobacillus Carrying Medium (LCM, Efthymiou & Hansen, J. Infect. Dis., 110:258–267, 1962) or Rogosa, is incubated for about 40 hours at 37° C., 50 ml is inoculated into 500 ml LCM, is incubated about 40 hours at 37° C., 500 ml is inoculated into 5 liters, is incubated about 25–30 hours at 37° C., is centrifuged at 10000 rpm for 10 minutes, is washed once in a physiological salt solution, the pellet is dissolved in about 1 liter of physiological salt solution.

This amount is estimated to be sufficient for about 400–500 l of oatmeal gruel. Cultivation media are not optimized. Rogosa worked better than LCM, possibly due to a better buffer function. 2% glucose was added to LCM. The same procedure can be used for producing the other Lactobacillus strains.

Colonization of *Lactobacillus plantarum* in vivo

In order to evaluate the ability to colonize in vivo 12 healthy volunteers were for 10 days given 100 ml liquid oat meal gruel containing $8 \times 10^7$ CFU/g freeze dried Lactobacillus strain as described in WO 93/01823. *Lactobacillus plantarum* 299 could be found in a dominating position on the intestinal mucosa 10 d after the completion of the administration.

In another test the ability of the strains *L. plantarum* 105 and 107 to colonize was tested. A freeze dried preparation containing $1.5 \times 10^9$ CFU of each test strain was ingested once a day for 8 days. Biopsies were taken from rectum one day before administration was started and one and eight days after the administration was terminated. In addition biopsies were also taken from jejunum. None of the administrated strains were reisolated, from Rogosa plates, eight days after the end of the administration.

Hemagglutination Test

In order to investigate whether the adhesins of the Lactobacillus strains resembled the adhesins for the mannose-containing receptors within the Enterobacteriaceae family, for instance occurring in *E. coli* strains, which are associated with type 1 fimbriae and mediate binding to colonic epithelial cells, hemagglutination tests were performed with erythrocytes of different origin.

Washed bacteria were suspended at $2 \times 10^{10}$/ml in PBS, and twofold dilutions of bacterial suspensions were mixed on microscope slides with equal volumes of 3% erythrocyte suspensions in PBS, or PBS containing 100 mM of methyl-α-D-mannoside. The slides were tilted gently at regular intervals, and agglutination was read after 15 minutes by the naked eye and using bright light microscopy at 250× magnification. The reciproc of the highest dilution of the bacterial suspension giving visible agglutination within 15 minutes was recorded as the agglutination titre.

The membrane-bound glycoproteins of erythrocytes contain mannose, and E. coli with mannose-specific adhesins agglutinate a wide range of erythrocytes in a mannose-sensitive manner.

The L. plantarum strains belonging to the genetic group 1c agglutinated erythrocytes from man, guinea pig, chicken, cat, dog, mouse, rat, rabbit, horse and pig, but more seldom sheep or bovine erythrocytes. With the exception of sheep and ox erythrocytes, the agglutinations were completely inhibited, or much reduced by methyl-α-D-mannoside. A weak mannose-sensitive hemagglutination was seen in some strains of the 1b group, whereas other genetic groups were negative.

The mannose-sensitive hemagglutination (MSHA) of L. plantarum much resembled that of E. coli, but some differences were observed. Thus with L. plantarum, chicken erythrocytes gave the highest MSHA titres, whereas horse erythrocytes were one of the least active erythrocyte species. With E. coli, on the other hand, horse erythrocytes gave the highest titres, slightly higher than chicken erythrocytes. Guinea pig erythrocytes showed a comparatively strong hemagglutinating activity with both L. plantarum and E. coli, whereas human erythrocytes were of low activity compared with other erythrocyte species for E. coli, but comparatively active in agglutination with L. plantarum.

Adherence to HT-29 Cells

Different Lactobacillus strains were tested for their ability to adhere to intestinal epithelial cells of human colonic carcinoma cell-line HT-29 (method as described by Wold, A, et al, Infection and Immunity, October 1988, p. 2531–2537). Cells of the human adenocarcinoma cell line HT-29 were cultured in Eagle's medium supplemented with 10% fetal calf serum, 2 mM L-glutamine and 50 μg/ml of gentamicin (Sigma Chemical Co., Saint Louis, Mo., USA). A few days after the cells had reached confluence they were detached with EDTA-containing buffer (0.54 mM), washed and suspended in Hank's balanced salt solution (HBSS) at $5\times10^6$/ml. The bacteria were harvested, washed and suspended in HBSS at $5\times10^9$/ml (2× an optical density of 1.5 at 597 nm). Cells, bacteria and HBSS were mixed in the ratio 1:1:3 and incubated with end-over-end rotation for 30 minutes at 4° C. The cells were washed once with ice cold PBS and fixed with neutral buffered formaline (Histofix, Histolab, Göteborg, Sweden). The number of bacteria attached to each of at least 40 cells was determined using interference contrast microscopy (500× magnification, Nicon Optophot, with interference contrast equipment, Bergström Instruments, Göteborg, Sweden) and the mean number of bacteria per cell was calculated. To test inhibition of adherence 1.5% of different monosaccharides (glucose, mannose, methyl-α-D-mannoside) was included in the adherence assay. The results are given in Table 2 below, in which the headlines, besides strain and genetic group, are as follows:

HT-29 VH is the mean value of the number of bacteria/cell; the number of experiments is stated within brackets;

α-methyl mannoside, mannose, and glucose, respectively, refer to the mean value of the number of bacteria/cell in the presence of α-methyl mannoside, mannose and glucose, respectively; the number of experiments is stated within

TABLE 2

| Strain | | Genetic group | HT-29 VH | α-methyl mannoside | mannose | glucose | n | d | p |
|---|---|---|---|---|---|---|---|---|---|
| 299v | L. plantarum | 1c | 11.2 (9) | 5.9 (9) | 8.3 (4) | 11.4 (6) | 9 | 5.3 | 0.004 |
| 299 | L. plantarum | 1c | 10.7 (8) | 4.9 (8) | 11.6 (3) | 10.6 (5) | 8 | 5.8 | 0.002 |
| 79 | L. plantarum | 1c | 11.7 (8) | 5.7 (8) | 6.8 (3) | 10.7 (5) | 8 | 5.9 | <0.0001 |
| 105 | L. plantarum | 1c | 10.8 (7) | 7.8 (7) | 9.8 (2) | 10.3 (4) | 7 | 3.0 | 0.15 |
| 107 | L. plantarum | 1c | 10.3 (7) | 6.9 (7) | 10.8 (2) | 15.3 (4) | 7 | 3.4 | 0.01 |
| 386 | L. plantarum | 1c | 5.8 (4) | 4.6 (4) | 7.0 (4) | 7.6 (4) | 4 | 1.2 | 0.59 |
| 275 | L. plantarum | 1c | 1.6 (3) | 1.3 (3) | 2.9 (3) | 3.1 (3) | 3 | 0.3 | 0.52 |
| 36E | L. plantarum | 1b | 6.0 (6) | 6.6 (6) | 7.7 (2) | 3.5 (2) | 6 | −0.6 | 0.58 |
| 256 | L. plantarum | 1b | 4.9 (6) | 4.5 (6) | 7.7 (3) | 9.8 (6) | 6 | 0.4 | 0.74 |
| 125 | L. plantarum | 1c | 8.7 | 2.9 | — | — | 3 | — | 0.0036 |
| ATCC14917 | L. plantarum | 1b | 5.6 (6) | 6.2 (3) | 1.9 (1) | 9 (1) | 3 | −0.6 | 0.70 |
| So5 | L. plantarum | | 1.3 (1) | 1.6 (1) | 3.5 (1) | 2.7 (1) | | | |
| ATCC8014 | L. plantarum | | 4.8 (5) | 1.0 (1) | 5.0 (1) | 5.0 (1) | | | |
| 98 | L. plantarum | 1b | 0.2 (5) | 0 (1) | | | | | |
| 53 | L. plantarum | 1a | 0.4 (5) | 0 (1) | | | | | |
| 97M2 | L. plantarum | | 6.4 (5) | 7.7 (2) | | | 2 | −0.2 | 0.70 |
| 97 | L. plantarum | 1a | 1.2 (4) | 6.7 (1) | | | | | |
| 101 | L. plantarum | 1a | 0.3 (1) | 1.0 (1) | 4.2 (1) | 3.8 (1) | | | |
| 120 | L. plantarum | | 0 (4) | 0 (1) | | | | | |
| 44 | L. plantarum | | 3.1 (1) | 6.7 (1) | 9.7 (1) | 6.5 (1) | | | |
| 8704:3 | L. fermentum | | 2.8 (3) | 10.9 (1) | | | | | |
| BR | L. reuteri | | 5.3 (4) | 13.6 (1) | | | | | |
| 108 | L. reuteri | | 0.3 (4) | 0 (1) | | | | | |
| 1063 | L. reuteri | | 2.5 (4) | 12.1 (1) | | | | | |
| 1068 | L. reuteri | | 2.2 (1) | 3.3 (1) | | | | | |
| 1044 | L. reuteri | | 1.7 (4) | 2.6 (2) | | | | | |
| M90 | L. reuteri | | 4.0 (4) | 1.3 (1) | 2.7 (1) | 4.0 (1) | | | |
| 8557:1 | L. reuteri | | 2.0 (4) | 4.1 (1) | | | | | |
| 8557:3 | L. reuteri | | 0.8 (4) | 0.8 (1) | | | | | |
| DSM20016T | L. reuteri | | 5.0 (3) | 13.8 (1) | | | | | |

TABLE 2-continued

| Strain | | Genetic group | HT-29 VH | α-methyl mannoside | mannose | glucose | n | d | p |
|---|---|---|---|---|---|---|---|---|---|
| R2LC | L. reuteri | | 0 (3) | 1.15 (1) | 0.3 (1) | 0.8 (1) | | | |
| 294 | L. agilis | | 0.7 (3) | 2.4 (1) | | | | | |
| 271 | L. rhamnosus | | 0 (2) | | | | | | | brackets;

n is the number of paired values in comparing adherence with and without α-methyl mannoside;

d is the mean difference with and without α-methyl mannoside; positive=inhibition with the mannoside;

p is p-value for the comparison; Student's T-test for paired values.

From these results can be seen that the first five strains of Lactobacillus show a strong adherence to HT-29 cells in vitro, which adherence is inhibited by the sugar α-methyl mannoside.

This adherence test was repeated with the *Lactobacillus plantarum* strains as well as five *Escherichia coli* strains. Four wild type strains were isolated from the rectal flora of Pakistani infants and identified as *E. coli* by biotyping, as described by Bettelheim, M. F., et al., J. Med. Microbiol. 2:225–236, 1969. The *E. coli* strains were cultured overnight at 37° C. in static Luria broth containing 0.1% $CaCl_2$ to promote the expression of type 1 fimboriae with mannose-specific adhesins. The transformant strain *E. coli* 506 MS, expressing type 1 fimbriae and mannose-specific adhesins was cultured on tryptic soy agar containing 25 μg of chloram-phenicol/ml. The *L. plantarum* strains were cultured on Rogosa agar for 24 h aerobically at 37° C.

To test inhibition of adherence the following monosaccharides were included at a final concentration of 60 mM in the adherence assay: D-glucose (USB, Cleveland, Ohio, USA), methyl-α-D-glucoside (Sigma), D-mannose (Merck, USA), N-acetyl-glucosamine (USB), N-acetyl-galactosamine (USB) and N-acetyl-neuraminic acid (sigma).

The *L. plantarum* strains 299 and 299v which had previously been shown to colonize human volunteers were shown to adhere to HT-29 cells to a moderate degree (approximately 10 bacteria/cell). This was also true for all but one of the other *L. plantarum* strains belonging to the genetic group 1c. Methyl-α-D-mannoside reduced the adherence of these strains by 45–73%. A lower degree of adherence (2–5 bacteria/cell) was seen among strains in group 1b. Their adherence was reduced by methyl-α-D-mannoside by 33–58%. Other *L. plantarum* strains which did not belong to the genetic groups 1b or 1c adhered in low numbers, and their adherence was not inhibited by methyl-α-D-mannoside.

D-mannose also reduced the adherence of *L. plantarum* 299 and 299v, but to a lesser degree than methyl-α-D-glucoside. None of the other monosaccharides tested, i.e. D-glucose, methyl-α-D-glucoside, L-fucose, galactose, N-acetyl-glucosamine, N-acetyl-galactosamine and N-acetyl-neuraminic acid, inhibited the adherence of *L. plantarum* 299 or 299v to HT-29 cells.

The *E. coli* strains with mannose-specific adhesins tested adhered at a level of 15–45 bacteria/cell. The adherence of *E. coli* 506 MS was inhibited to a similar degree (94%) by both methyl-α-D-mannoside and D-mannose.

The results of the adherence of bacteria to HT-29 cells after incubation in presence or absence of 60 mM metyl-α-D-mannoside, washing and calculating the mean values from 3 experiments (for *E. coli* 345, 253, 810 and 476 only one experiment) are given in Table 3 below.

Binding to D-mannose Immobilized on Igarose Beads

Tests for binding of bacteria to D-mannose-coated agarose beads were performed according to Sanchez and Jonson (APMIS., 1990, 98:353–357), with slight modifications. Washed bacteria, suspended at $10^{10}$/ml in PBS were mixed on microscope slides with equal volumes of a 1:4 suspension in PBS of commercial agarose beads containing covalently linked D-mannose (Agarose-p-aminophenyl-α-D-mannopyranoside, Sigma, St. Louis, USA) or plain agarose beads (4% beaded agarose, PL-Biochemical, Milwaukee, Wis., USA). The slides were tilted for 2 minutes and thereafter observed in an interference contrast microscope (500× magnification, Nicon Optiphot). The observation of bacteria adhering to the mannose coated beads, in the absence of binding to plain agarose beads was considered a positive reaction. The results of this test are given in Table 3. The binding to the mannose-coated agarose beads was estimated as follows:

No difference in binding compared with control beads lacking mannose;
  Bacteria are covering 50% or more of the surface area of the beads in a thin layer;
    Bacteria are covering the whole surface area of the beads in a thick layer, sometimes appearing as a multilayered coating.

Binding to D-mannose coated agarose beads was observed with all *L. plantarum* strains which adhered to HT-29 cells and agglutinated erythrocytes in a mannose-sensitive manner, that is all strains belonging to group 1c, and ATCC 14917$^T$, 256 and 36E in group 1b. Most positive strains reacted strongly with the mannose-coated agarose beads; weak reactions were observed with L plantarum 275 and ATCC 14917$^T$ and 256. All *L. plantarum* strains which had been negative for mannose-sensitive adherence were also negative with the mannose coated beads except for *L. plantarum* 97 belonging to subgroup 1a. This strain had, however, occasionally displayed mannose-sensitive adherence in other experiments.

*E. coli* 506 MS bound at approximately the same level as the strongly positive *L. plantarum* strains.

TABLE 3

| Strain | Genetic group | Adhering bacteria/cell (mean ± SD) | | | Binding to mannose-coated agarose beads |
|---|---|---|---|---|---|
| | | HBSS | +methyl-mannoside | p | |
| *L. plantarum* | | | | | |
| 97 | 1a | 1.2 ± 0.9 | 1.5 ± 0.9 | | + |
| 101 | 1a | 0.5 ± 0.4 | 1.1 ± 0.8 | | − |
| 53 | 1a | 0.8 ± 0.4 | 2.0 ± 0.9 | | − |
| ATCC 14917$^T$ | 1b | 5.2 ± 0.8 | 2.2 ± 0.7 | 0.070 | + |
| 256 | 1b | 3.7 ± 0.3 | 1.8 ± 0.5 | 0.020 | + |
| 36E | 1b | 2.4 ± 1.8 | 1.6 ± 1.5 | 0.17 | ++ |
| 98 | 1b | 0.6 ± 0.6 | 0.4 ± 0.2 | | − |
| 299 (=DSM6595) | 1c | 8.1 ± 1.1 | 3.8 ± 0.5 | 0.029 | ++ |
| 299v (=DSM9843) | 1c | 11.7 ± 1.4 | 3.4 ± 0.5 | 0.017 | ++ |
| 107 | 1c | 11.9 ± 1.7 | 3.7 ± 0.5 | 0.020 | ++ |
| 105 | 1c | 13.3 ± 5.0 | 3.8 ± 0.4 | 0.093 | ++ |
| 79 | 1c | 12.1 ± 3.5 | 3.3 ± 0.4 | 0.056 | ++ |
| 125 | 1c | 8.7 ± 1.6 | 2.9 ± 1.7 | 0.0036 | ++ |
| 275 | 1c | 2.9 ± 0.3 | 1.6 ± 0.2 | 0.038 | + |
| 386 | 1c | 11.6 ± 2.8 | 4.1 ± 0.9 | 0.021 | ++ |
| So5 | | 2.2 ± 0.4 | 4.6 ± 2.2 | | − |
| ATCC 8014$^T$ | | 2.7 ± 1.0 | 4.5 ± 1.5 | | − |
| 120 | | 0.9 ± 0.6 | 0.8 ± 0.7 | | − |
| 44 | | 1.4 ± 1.2 | 1.6 ± 0.2 | | − |
| *E. coli* | | | | | |
| 345 | | 18.4 | 0.7 | | |
| 253 | | 45.4 | 2.7 | | |
| 810 | | 26.2 | 0.5 | | |
| 476 | | 16.3 | 1.7 | | |
| SO6 MS | | 34.5 ± 8.9 | 2.6 ± 0.9 | 0.020 | ++ |

Metaperiodate Oxidation and Enzymatic Treatment of Bacteria and HT-29 Cells

Washed bacteria or HT-29 cells were suspended in 0.01M metaperiodate (Merck, USA) in 0.1 M citrate-phosphate buffer, pH 4.5. Bacteria were incubated at 37° C. for one hour, whereas HT-29 cells were incubated at room temperature for 15 or 30 minutes. After incubation, bacteria or cells were spun down, washed twice in PBS, and resuspended in HBSS. Control incubations were performed with 0.01 M sodium iodate (Mallinckrodt Chemical Works, Saint Louis, Mo., USA) in the same buffer as above, or with buffer alone.

Washed bacteria or HT-29 cells were suspended in PBS containing 2 mg/ml of Proteinase K (15 units/mg, Sigma) or in PBS alone, incubated at 37° C. for one hour and washed and resuspended as described above.

Treatment of HT-29 cells with periodate for 15 or 30 minutes led to cell destruction; only 5–10% of the cells remained after treatment and the following adherence assay. Still, mannose-sensitive adherence of *L. plantarum* to cells that had been treated for 15 minutes remained high (p=0.41 in relation to the buffer control), whereas cells that had been treated for 30 minutes did not bind *L. planatarum* in a mannose-sensitive manner (p=0.033 in relation to buffer control) and periodate treatment for 30 minutes almost abolished the adherence (p=0.0005 in relation to buffer control, p=0.0067 in relation to iodate control). Periodate oxidation of bacterial cell surface carbohydrates did not much affect binding.

Treatment of *L. plantarum* with Proteinase K completely abolished their ability to adhere to HT-29 cells (p=0.0008, Table 5), whereas no reduction in the adherence of *E. coli* 506 MS was observed after treatment of the bacteria with this enzyme. Proteinase K treatment of HT-29 cells had no clear effects on the adherence of *L. plantarum* 299v (p=0.36), but tended to reduce the adherence of the type 1-fimbriated *E. coli* 506 MS (p=0.15, Table 4).

These experiments confirm that the cell-bound receptor is of a carbohydrate nature and that a protein structure on the bacterial cell surface is involved in the adhesion to said receptor.

Adherence of *Salmonella typhimurium* to HT-29 Cells

Salmonella is a major pathogen in diarrhoeal disease. Many Salmonella strains carry type 1 fimbriae, which can be detected by a mannose-sensitive hemagglutination.

A Salmonella strain derived from a patient with gastrointestinal disease, *Salmonella typhimurium* 11014, displaying a mannose-sensitive agglutination of erythrocytes, was selected for this adherence test. The Salmonella strain was labelled with the fluorescent probe FITC (Fluorescein isothiocyanate, Sigma) by incubating bacteria and FITC in carbonate buffer, pH 9.6, overnight in the cold. The bacteria were washed 3 times before used in the adherence assay.

For adherence, 0.1 ml HT-29 cells ($5.10^6$/ml) were mixed with $5.10^8$ fluorescent Salmonella and $5.10^8$ unlabelled *Lactobacillus plantarum* 299 or 299v. The mixture was incubated for 30 min with end-over-end rotation in the cold. After washing the cells, adhering bacteria were counted in a microscope with equipment for fluorescence detection. The results are presented in the table below.

TABLE 4

| | Adherence to HT-29 cells |
|---|---|
| | Number of bacteria/cell |
| Salmonella typhimurium 11014 | 25 |
| Salmonella typhimurium 11014 + 2.5% methyl-α-D-mannoside | 1 |

TABLE 4-continued

Adherence to HT-29 cells

| | Number of bacteria/cell |
|---|---|
| Salmonella typhimurium 11014 + Lactobacillus plantarum 299 | 7 |
| Salmonella typhimurium 11014 + Lactobacillus plantarum 299v | 12 |

It is evident from the above Table that the Salmonella strain adhered to human colonic cells, that is HT-29 cells, via a mannose-specific mechanism. This mannose-sensitive adherence could be blocked by Lactobacillus plantarum to a high degree. The bacteria were present simultaneously, in equal amounts.

It is likely that if the Lactobacillus strain was added before the pathogenic strain it would occupy the sites for the pathogenic bacteria carrying mannose-specific adhesins, thereby making it impossible for them to become established and cause disease.

Acute liver failure has a high mortality rate and a significant proportion of the mortality can be attributed to the high incidence of sepsis. In critically ill or immuno-compromised patients most infections are caused by the patient's own microflora and many patients dying of sepsis or multiple organ failure have enteric bacteria for which no septic focus is identified indicating that these infections may have originated from the gut. Because of the high frequency of clinically significant bacterial sepsis during fulminant hepatic failure the possibility of prophylactic treatment has been raised. In acute liver failure or after major liver surgery there is an increased bacterial translocation from the gut, which may explain some of the infectious complications seen in these conditions. In order to elucidate the mechanisms and find possible preventive measures the following model was designed.

Test in Rats
Effect of Lactobacilli Supplementation in Acute Liver Injury Failure The aim of this experiment is to study the effect of rectal supplementation of different strains of Lactobacillus on the extent of bacterial translocation in an acute liver injury model. The influence of such an administration on the number of Enterobacteriaceae in colon and cecum is also investigated.

Male Sprague-Dawley rats with a weight range of 200–300 g were divided into 7 groups of six animals: normal, control acute liver injury (ALI), supplemented Lactobacillus reuteri R2CL (SR), supplemented Lactobacillus rhamnosus 271 (SS), supplemented Lactobacillus plantarum 299v (SP), supplemented Lactobacillus fermentum 8704:3 (SF), and supplemented Lactobacillus reuteri 108 (ST). All animals received normal rat chow (R3, Lactamin AB, Stockholm) and water ad libitum throughout the experiment and were kept at 12 hours light/dark cycle and 22° C. room temperature. The different Lactobacillus strains were administered rectally once daily for 8 days. The daily supplementation of the Lactobacillus strains was about $3 \times 10^9$ CFU per animal in 3 ml. Acute liver injury was induced in the 8th day by intraperitoneal injection of D-galactoseamine (Sigma Chemical Co., St Louis, USA), 1.1 g/kg body weight, which brings about an increased leakage of bacteria from the intestinal lumen to distant organs. In the acute liver control group, normal saline was supplemented daily for 8 days and the liver injury induced on the 8th day. Samples were collected 24 hours after the evocation of the liver injury. Under ether anaesthesia a laparotomy was performed through a midline incision under aseptic technique. Portal and aortic blood was collected for bacteriological tests. Samples from the caudate lobe of the liver and mesenteric lymph nodes (MLN) were obtained for bacteriological study; cecal and colonic contents for bacterial count.

In the bacteriological analysis tissue samples were placed in 5 ml of sterile transport medium. The samples were placed in ultrasonic bath for 5 minutes and swirled on Chiltern (Terma-Glas, Sweden) for 2 minutes. Total aerobic plate count was made by placing 1.0 ml of the sample on brain heart infusion agar BHI (Oxoid) and incubated at 37° C. for 3 days. Total anaerobic plate count was made by placing the samples on BHI and incubating under anaerobic condition at 37° C. After 3 days the number of colonies formed on each plate were counted and corrected for the weight of the original tissue. Tissue samples were expressed per gram of tissue. All values are presented as mean±SEM. The results are statistically evaluated using unpaired Student t test. A probability level less than 0.05 was considered significant ($p<0.05$).

TABLE 5

Bacterial translocation to the liver and MLN

| Group | Liver, CFU/g | MLN, CFU/g |
|---|---|---|
| ALI | 5300 ± 1750 | 4940 ± 2060 |
| SR | 880 ± 530* | — |
| SS | 1460 ± 990* | 180 ± 40* |
| SP | 20 ± 10** | — |
| SF | 160 ± 80** | 70 ± 30* |
| ST | 930 ± 850* | 20 ± 5* |

*denotes $p < 0.05$,
**denotes $p < 0.01$

Pretreatment of the rats with Lactobacillus plantarum 299v significantly reduced the bacterial translocation from the gut and improved the liver status.

The bacterial microflora was investigated by taking samples from cecum and colonic content which were immediately placed in 5 ml sterile transport medium and placed in ultrasonic bath and swirled on chiltern as before. Viable Enterobacteriaceae counts were obtained from violet red-bile-glucose agar VRBG (Oxoid) that was incubated aerobically at 37° C. for 24 hours.

TABLE 6

Enterobacteriaceae count in colon and cecum

| Group | CFU/g in colon | CFU/g in cecum |
|---|---|---|
| Normal | 4.1 ± 1.7 | 6.5 ± 0.3 |
| ALI | 6.8 ± 0.2 | 4.9 ± 0.1 |
| SR | 6.7 ± 0.2 | 5.1 ± 0.2 |
| SS | 5.1 ± 1.1 | 3.5 ± 1.1 |
| SP | 4.7 ± 1.0* | 4.3 ± 0.2 |
| SF | 1.9 ± 1.2** | 5.5 ± 0.2 |
| ST | 3.0 ± 1.4 | 4.3 ± 0.1 |

*denotes $p < 0.05$,
**denotes $p < 0.01$

The above table shows that the Enterobacteriaceae count in colon as well as in cecum decreased in all the groups supplemented with Lactobacillus.

Clinical Test

Pro Viva (rose hip soup based on oats fermented with Lactobacillus plantarum 299v, Skånemejerierna Ekonomisk Förening, Malmö, Sweden) was given to 26 children suffering from acute gastroenteritis at the hospital of Szezecin, Poland, for a median period of 5.5 days. The product was given in an amount of 400 ml/d; 200 ml in the morning and 200 ml in the evening.

Before the treatment all children had between 3 and 9 loose stools per day, which after the treatment was reduced to a frequency of 1–2 stools per day. Six patients yielded pathogens in stool cultures before treatment, that is Salmonella in 3 children, enteropathogenic *E. coli* in 2 children, Enterobacter aeromonas and Giardia intestinalis in 1 child each. After treatment all these pathogens were absent from stool cultures. All of these pathogens with the exception of Giardia intestinalis are known to possess type 1 fimbriae and adhere via mannose-specific mechanisms to intestinal epithelial cells. It is likely that the capacity of *Lactobacillus plantarum* 299v to compete with the pathogens for binding sites on mannose-containing glycoproteins on epithelial cells, or in the mucus layer, was responsible for the vanishing of these bacteria from the stool cultures after administration of *Lactobacillus plantarum*.

Conclusion

The wide-spread occurrence of mannose-specific adhesins among Gram-negative bacteria residing in the intestinal tract suggests that these adhesins are of importance for the intestinal colonization. A mannose-specific adhesin has never before been identified in a Gram-positive species, such as *Lactobacillus plantarum*. It can be assumed that the ability to adhere to mannose containing receptors is of importance for the pronounced colonizing ability of this bacterium. However, also bacteria which lack the ability to adhere to mucosal receptors can be good colonizers of the intestinal tract, e.g. the strain 271, which does not adhere to intestinal epithelial cells.

The ability to bind to mannose-containing receptors on the epithelium likely provides the *Lactobacillus plantarum* with a special ability to counteract the effect of pathogenic bacteria. Firstly, it is a good intestinal colonizer. Secondly, it will compete with the pathogenic bacteria for receptor sites which are important for the colonizing ability of the pathogenic bacteria, i.e. the mannose-containing mucosal receptors, Thirdly, by binding to receptors present on intestinal epithelial cells, the *Lactobacillus plantarum* will be able to influence the immediate micromilieu of the epithelial cells. Thus, the change in micromilieu afforded by lactobacilli will be more likely to affect the epithelial cells than if the lactobacillus bacteria resides in a place more distant from the epithelium. Fourthly, by binding to mannose-containing receptors on the epithelial cells, *Lactobacillus plantarum* will be able to hinder the attachment of pathogenic bacteria, thereby reducing their ability to deliver toxic or otherwise irritating substances directly on the epithelial cells, which is often a prerequisite for the pathogenic action of these bacteria.

What is claimed is:

1. A method for treating acute gastroenteritis comprising administering to a patient having acute gastroenteritis and having an intact epithelium an effective amount of a *Lactobacillus plantarum* having a mannose-specific adhesin to reduce gastroenteritis, wherein the *Lactobacillus planatarum* is *Lactobacillus planatarum* 299v, deposited under the accession No. DSM9843 and wherein the acute gastroenteritis is caused by bacteria which express type 1 fimbriae and are selected from the group consisting of Klebiella, Enterbacter, Proteus, Samonella, Shigella, and *Escherichia coli*.

2. The method of claim 1, wherein the *Lactobacillus plantarum* has the property of adhering to D-mannose-coated agarose beads.

3. The method of claim 1, wherein the *Lactobacillus plantarum* further comprises a pharmaceutically acceptable carrier.

4. The method of claim 1, wherein the bacteria are *Escherichia coli* expressing type 1 fimbriae.

5. A method of treating urinary tract infections, comprising:

administering to a patient in need of treatment for a urinary tract infection an effective amount of *Lactobacillus plantarum* having a mannose-specific adhesin to reduce the infection of the urinary tract, wherein the *Lactobacillus plantarum* is *Lactobacillus plantarum* 299v, deposited under the accession No. DSM9843 and wherein the urinary tract infection is caused by a bacteria selected from the group consisting of *Escherichia coli*, Enterobacter, Klebiella and Proteus.

* * * * *